(12) United States Patent
Sandra et al.

(10) Patent No.: US 9,061,281 B2
(45) Date of Patent: Jun. 23, 2015

(54) SYSTEM FOR CARRYING OUT A SAMPLE PREPARATION

(75) Inventors: Patrick Sandra, Marke (BE); Bart Tienpont, Zwevegem (BE); Frank David, Brugge (BE); Tom Sandra, Bellegem (BE); Koen Sandra, Bellegem (BE)

(73) Assignee: Gerstel Systemtechnik GmbH & Co. KG, Mulheim (DE)

(*) Notice: Subject to any disclaimer, the term of this patent is extended or adjusted under 35 U.S.C. 154(b) by 77 days.

(21) Appl. No.: 13/700,711

(22) PCT Filed: May 24, 2011

(86) PCT No.: PCT/EP2011/002562
§ 371 (c)(1),
(2), (4) Date: Dec. 11, 2012

(87) PCT Pub. No.: WO2011/151026
PCT Pub. Date: Dec. 8, 2011

(65) Prior Publication Data
US 2013/0078165 A1    Mar. 28, 2013

(30) Foreign Application Priority Data
May 29, 2010  (DE) .................. 10 2010 022 016

(51) Int. Cl.
*B01L 3/14*  (2006.01)
*B01L 3/00*  (2006.01)
(Continued)

(52) U.S. Cl.
CPC ............ *B01L 3/50825* (2013.01); *B01D 15/12* (2013.01); *G01N 1/02* (2013.01); *G01N 1/125* (2013.01); *G01N 30/06* (2013.01); *G01N 30/18* (2013.01)

(58) Field of Classification Search
CPC .............................. G01N 21/783; B01D 15/00
USPC ....................................... 422/550; 435/288.6
See application file for complete search history.

(56) References Cited

U.S. PATENT DOCUMENTS 2,231,322 A * 2/1941 Cathcart .................... 422/306
3,179,499 A   4/1965 Hampton
(Continued)

FOREIGN PATENT DOCUMENTS

DE    1846022 U    1/1962
DE    1846022 U    2/1962
(Continued)

OTHER PUBLICATIONS

Office Action for German priority application DE 10 2010 022 016.7 filed May 25, 2010, two pages.
(Continued)

*Primary Examiner* — Dennis M White
*Assistant Examiner* — Bryan Kilpatrick
(74) *Attorney, Agent, or Firm* — Kilpatrick Townsend & Stockton LLP

(57) ABSTRACT

The invention relates to a system for carrying out a sample preparation for an analysis apparatus, in particular a chromatograph, comprising a sample vessel (1), which can be closed by a self-sealing cover and has a sample compartment (31) for receiving a substance to be examined, further comprising a holder, which has a heating wire coil (13) and into which the sample vessel (1) with the sample compartment (31) can be inserted for heating the substance to be examined, and further comprising a power supply for the heating wire coil (13) which is based on a constant current source and is controlled proportionally by pulse width modulation.

4 Claims, 5 Drawing Sheets

Figure 3:
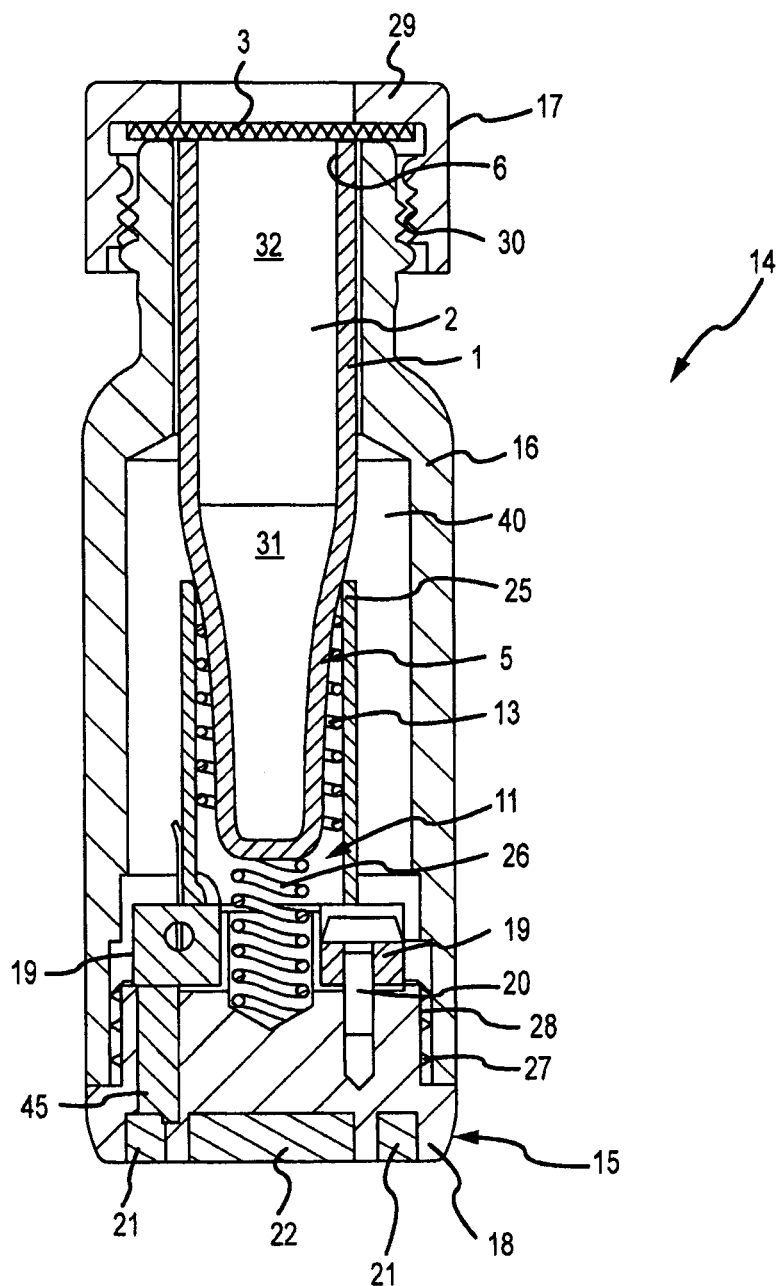

(51) Int. Cl.
*G01N 30/06* (2006.01)
*G01N 30/18* (2006.01)
*B01D 15/12* (2006.01)
*G01N 1/02* (2006.01)
*G01N 1/12* (2006.01)

(56) References Cited

U.S. PATENT DOCUMENTS

| | | | |
|---|---|---|---|
| 5,782,964 A | 7/1998 | Mustacich | |
| 6,907,796 B2 * | 6/2005 | Bremer et al. | 73/863.11 |
| 2007/0137320 A1 * | 6/2007 | Bremer et al. | 73/864.01 |
| 2007/0140904 A1 * | 6/2007 | Bremer et al. | 422/68.1 |
| 2008/0026288 A1 * | 1/2008 | Marple et al. | 429/178 |

FOREIGN PATENT DOCUMENTS

| | | |
|---|---|---|
| DE | 1598436 A | 11/1965 |
| DE | 19817016 A1 | 4/1998 |
| DE | 19720687 C1 | 7/1998 |
| EP | 1798551 A1 | 6/2007 |
| JP | S57-086454 | 12/1980 |
| JP | 2003-083978 A1 | 3/2003 |
| JP | 2007-163492 A | 6/2007 |

OTHER PUBLICATIONS

English translation of Office Action corresponding to Japanese Patent Application No. 2013-512783, Jan. 15, 2015.

* cited by examiner

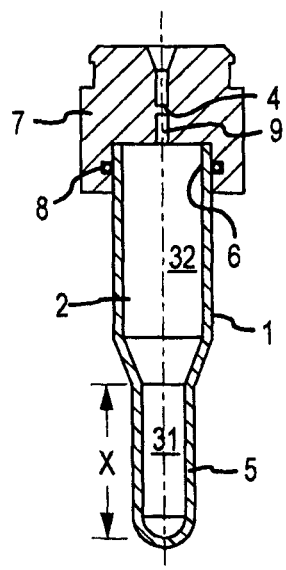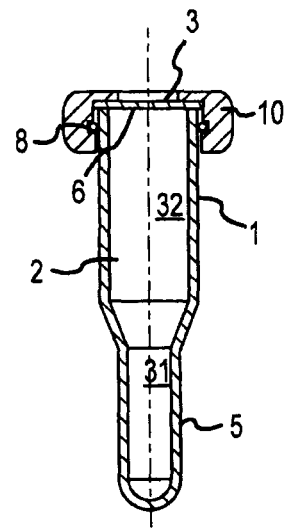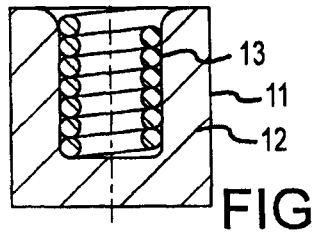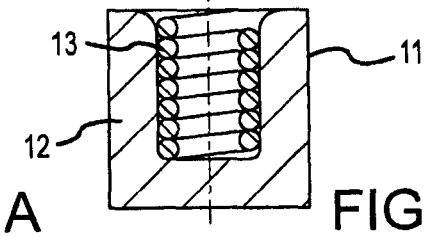
FIG.1A  FIG.2A
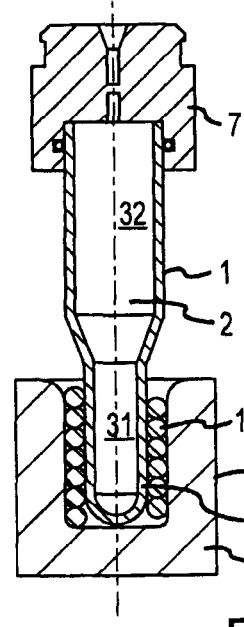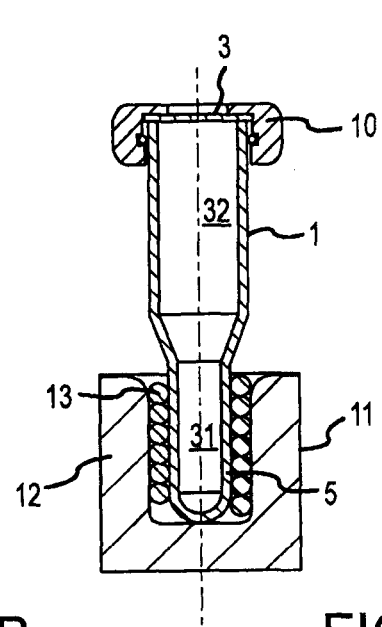
FIG.1B  FIG.2B

SYSTEM FOR CARRYING OUT A SAMPLE PREPARATION

The invention relates to a device for preparing a sample for chromatographic separation methods.

Chromatographic separation methods are some of the most important analysis methods for the qualitative and quantitative determination of sample constituents. The efficiency of the separation technique can generally be increased by suitable sample preparation. For maximum performance in precision, repeatability and sample throughput, the user only achieves this when he can automate as many sample preparation steps as possible.

DE-A 1 773 141 discloses a method for sampling in gas analysis apparatus, in particular gas chromatographs, in which a sample vessel is partially filled with a liquid or solid substance to be examined and subsequently provided with a self-sealing membrane. By adjusting the temperature of the sample vessel, the volatile components are concentrated in the free internal space of the sample vessel. In order to take samples from this gas space, a sampling device is pushed through the membrane. The volatile constituents taken in this so-called headspace method are then examined by gas analysis.

In order to carry out the method automatically, various sample vessels are arranged in a row on a transport device which has stations where the sample vessels are subjected to a treatment. This includes the initiation of a chemical reaction of at least one sample component and transport of the sample vessel after a certain distance below an extraction device.

In the case of pyrolysis, metal scoops are filled with the substance to be examined, and these scoops are put into the sample vessels. The scoops may then be heated again at particular positions of the transport device, for example inductively. The most volatile pyrolysis products are examined in this case.

In order to prepare solid samples with the aid of pyrolytic decomposition for analysis by means of a gas chromatograph, it is generally known to decompose substances to be examined directly in the gas chromatographs (GC) input with air exclusion. According to common practice, the pyrolysis products are subsequently delivered onto the GC column, separated and measured.

As is known from DE 42 06 109 C2, the pyrolytic decomposition of chemical substances in analytical chemistry is also used for example in order, from solid high molecular weight substances, to obtain low molecular weight products which can be separated and identified by chromatographic separation methods. To this end, the substances to be examined are placed in metal scoops in a reactor housing. The metal scoops are heated in order to adjust a pyrolysis temperature. The reactor vessel is flushed by a carrier gas flow which carries the pyrolysis products into an analytical measurement device.

The thermal breakdown (pyrolysis, thermolysis) of semisolid and solid samples before chemical analysis of the resulting breakdown products is nowadays an extensively used sample preparation method for the identification or characterization of solid or semisolid samples. On the analytical scale, a sample, typically in the μg to mg range, is put into a small container or brought directly into contact with a heating medium. The sample is heated for a very short time to a temperature which allows thermochemical reaction of the sample.

The pyrolysis is generally carried out at temperatures of between 500° C. and 1400° C. The products of the thermal breakdown (pyrolysate) are then preferably analyzed by chromatographic separation methods, predominantly gas chromatography. In other cases, the pyrolysate is introduced directly into a detector, usually a mass spectrometer, for general characterization of the pyrolysate composition. The samples typically analyzed by pyrolysis are nowadays biological samples and environmental samples, or are found in artistic materials, in food and agricultural applications, in geochemistry and fuel sources, in forensics and synthetic polymers. Various chemical reagent products are furthermore available for the in-situ derivativization of polar pyrolysate compounds. Polar compounds, which give poor peak shapes in gas chromatography, can consequently be detected by modification of the pyrolysate compound structure. It is essential for the analytical pyrolysis that the pyrolysis temperature is attained as quickly as possible and that the temperature is maintained for a period of time defined by the user.

DE 198 17 016 A1 discloses a sampling tube comprising a sample, which can be fitted into a heating coil. DE 197 687 C1 discloses a pyrolysis tube in an induction coil. DE 1 846 022 U discloses a pyrolysis cell surrounded by a platinum spiral. DE 1 598 436 A discloses a heating resistor in a pyrolysis space.

It is therefore an object of the invention to provide a device for carrying out sample preparation, which improves the automated handling of the samples with thermochemical preparation thereof for analytical examination of the thermal breakdown products and optimizes the reproducibility of the sample preparation.

This object is achieved by the features of claim 1.

In this way, a device for carrying out sample preparation is provided, which allows advantageous heat treatment of the sample respectively to be examined. The sample vessel according to the invention forms a reaction space, which allows rapid heating of the sample.

Quantities of liquid may furthermore be introduced into the sample vessel, in order to be able to carry out chemical reactions before and/or after the heat treatment of the sample. The sample vessel is therefore preferably at the same time also a kind of test tube. The converted or broken down products/compounds may be dissolved in the sample vessel after the heat treatment.

What is essential for reproducibility and automatability is that the thermal process and optionally a dissolving process with or without chemical reaction before and/or after the thermal process can take place in the sample vessel. The injection system of the chromatography system or detection system as well as the separating column are not contaminated in the thermal process, since the withdrawal for the injection process takes place from the sample vessel. The thermochemical reaction in the sample vessel is carried out independently of the analysis process. Direct coupling with a chromatography system is not established.

A sample may be taken and directly stored in the sample vessel and sent to a laboratory for a thermochemical reaction, in particular a pyrolysis, for example without changing its nature. Microorganisms such as bacteria and fungi can therefore be cultured or harvested and put directly into a (sterilized) container. The thermochemically converted or pyrolytically broken down products may likewise be stored. The closed system limits the risk of contamination.

Preferably, a decentral interface based on a container is provided. This interface particularly preferably comprises a container arrangement having a module container, which is formed with an integrated heating element. An insertable container as a sample vessel is inserted into the module container. The module container can be closed by a cap with a septum (or injection stopper). This septum preferably simultaneously also covers the insertable container. Samples are put into the insertable container and the latter is then heated to a temperature which allows a thermochemical reaction, in particular a thermal breakdown (pyrolysis, thermolysis) of the sample. Gases and/or liquids can be injected into the insertable container as a sample vessel through the septum. The module container is consequently preferably an injection container (or vial) with an internal holder as a sample vessel.

The dimensions of a module container may be selected so that it can be transported and handled by the most commercially available robots and automatic sampling devices of chromatography equipment.

The sample vessel may be flushed with an inert or reactive gas before the heat treatment. After the heat treatment of the sample, the sample vessel may be allowed to cool.

A small quantity of solvent may furthermore be poured into the sample vessel, in order to dissolve the products of the thermal breakdown. This solution may be subjected to a chemical analysis, in particular by gas chromatography (GC), high-performance liquid chromatography (HPLC), supercritical fluid chromatography (SFC) or capillary electrophoresis (CE).

Further configurations and advantages of the invention may be found in the following description and the dependent claims.

The invention will be explained in more detail below with the aid of exemplary embodiments represented in the appended figures.

Figure 4A:
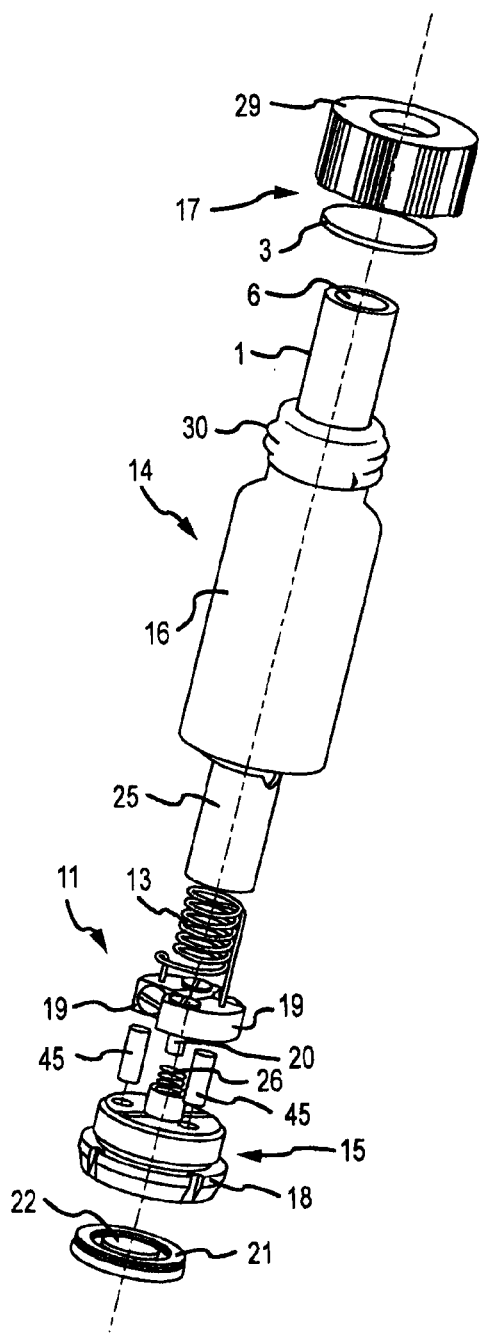
Figure 4B:
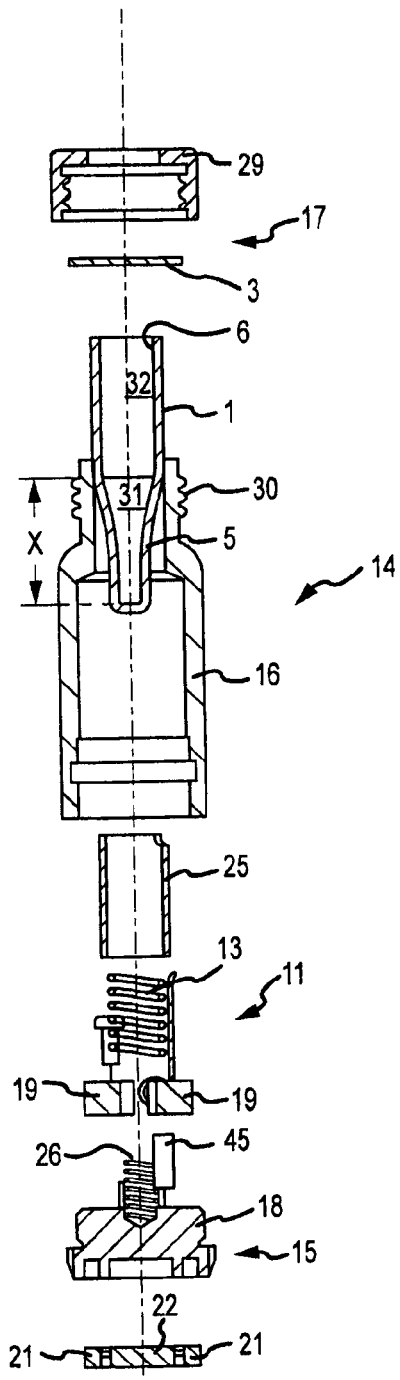
Figure 5:
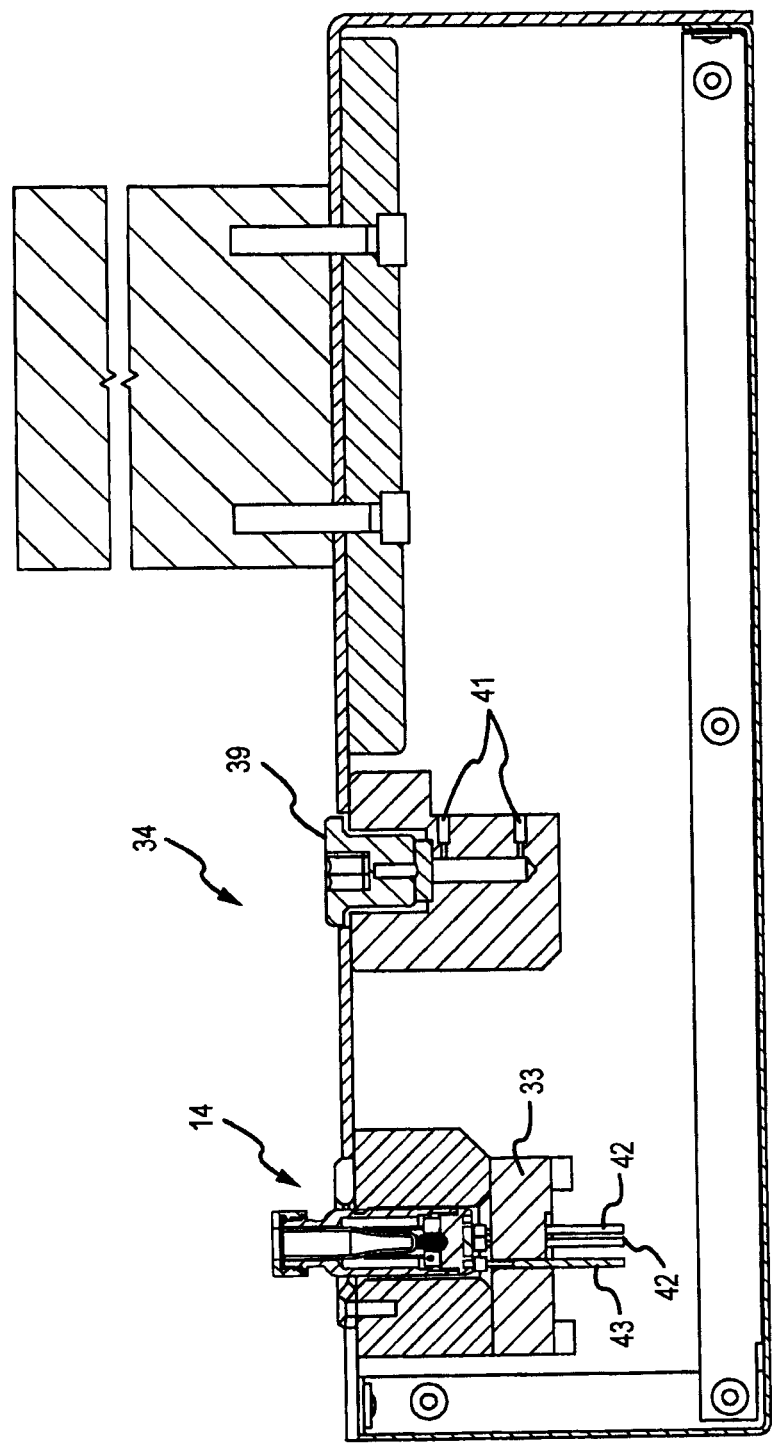
Figure 6:
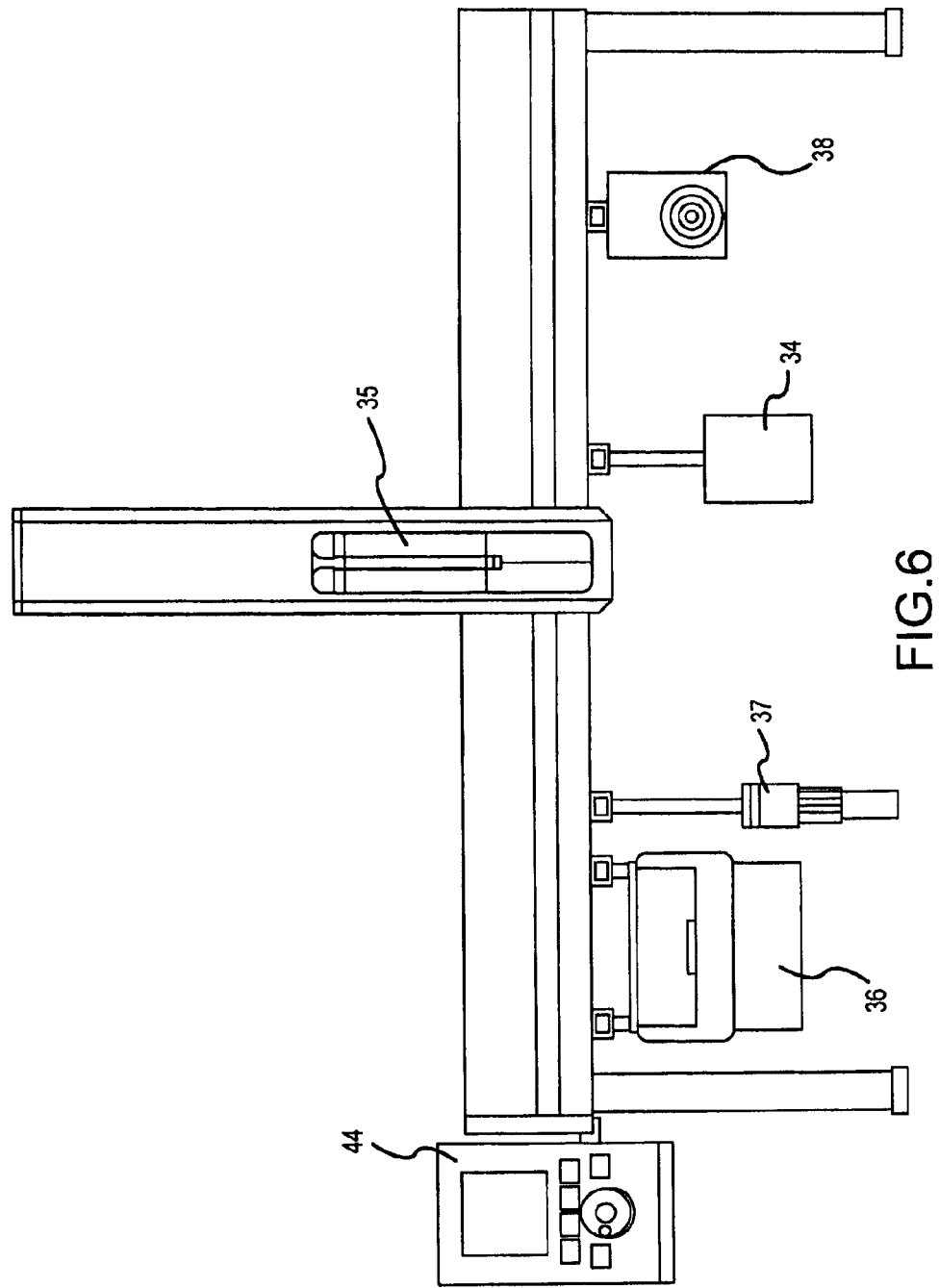

FIGS. 1A and 1B schematically show sections of a sample vessel comprising a holder according to a first exemplary embodiment, FIGS. 2A and 2B schematically show sections of a sample vessel comprising a holder according to a second exemplary embodiment, FIG. 3 schematically shows a section of a module container comprising an insertable container as a sample vessel, FIGS. 4A and 4B schematically show the module container comprising the insertable container as a sample vessel according to FIG. 1 in a perspective exploded representation and in longitudinal section thereof, FIG. 5 schematically shows a module container station, FIG. 6 schematically shows an automated sample preparation station.

The invention relates to methods for preparing samples for chromatographic separation methods and devices for carrying out sample preparation.

As represented in FIG. 1A, FIG. 1B, FIG. 2A, FIG. 2B, in the method according to the invention for preparing samples, a sample vessel 1 is used. This sample vessel 1 forms a cavity, which is filled with a substance to be examined as a core. The sample vessel 1 is preferably a hollow vessel, in particular a tubular container, for receiving substance to be examined. The substance to be examined is subjected to a thermochemical reaction in the sample vessel 1. The sample vessel 1 is only partially filled with the substance to be examined, or sample, through its opening on one side and is closed. The sample preferably consists of solid, semisolid or concentrated products. The sample vessel 1 is preferably closed with a septum 3 or a self-sealing separating wall 4.

The length and width of the sample vessel 1 are selected so that by the sample introduced, the quantity of which on the analytical scale usually lies in the μg to mg range, at most a sublength X of an internal space 2 of the sample vessel 1, or its cavity, is filled with the sample. The internal space 2 of the sample vessel 1 to this extent forms a sample compartment 31. Above this sublength X, the internal space 2 of the sample vessel 1 forms a headspace compartment, or an interior compartment 32, which may for example form a free interior section. In the headspace compartment 32, volatile components may be concentrated or gases may be flushed in, so that the headspace compartment 32 then forms a gas space, or gas compartment. As an alternative or in addition, the headspace compartment 32 may be filled with a solvent and/or a reagent, specifically before and/or after the thermochemical reaction of the sample. The headspace compartment 32 may then be used as a solvent compartment.

The width of the sample vessel 1 in the region of the sample compartment 31 preferably lies in a range of from 1 to 20 mm. The sample may fill the sample vessel 1 with a filling height. The substance to be examined may then accumulate in the sample vessel 1, in particular in the sample compartment 31, for example in the manner of a column or silo. The sample may alternatively also be introduced into the sample vessel 1 as liquid, one-piece solid body or agglomerate. Above the filling quantity or filling object, a free space region of the headspace compartment 32 extends, which may be filled with a gas or a liquid.

The substance to be examined, or sample, is subjected in the sample vessel 1 to a thermochemical reaction in which at least one sample component is converted into another substance. Preferably, this involves thermolysis or pyrolysis. The sample vessel 1 is therefore a reaction vessel for the sample preparation.

The products of the thermal conversion, or the thermal breakdown, are taken from the sample vessel 1 by an extraction device (not shown) for analytical examination. The sample vessel 1 is therefore a reaction vessel for the sampling.

The sample vessel 1 preferably comprises a shaft or a vessel constriction 5 as a cavity, into which the substance to be examined, or sample, is introduced in order to be subjected there to the thermochemical reaction. The shaft (or the vessel constriction) 5, which is at least partially filled with the substance to be examined, forms the sample compartment 31 and consequently preferably extends along the sublength X. The shaft 5 preferably forms a lower part of the sample vessel 1. The sample vessel 1 is then preferably shaped as a container with a selectable nominal width and a narrower cross section in the region of the shaft 5. The shaft 5 essentially forms a container neck of a container arranged standing on its head, which is open on one side at a container opening 6.

The sample vessel 1 is formed with an end open on one side at an opposite end to the shaft 5, here preferably the container opening 6, which is closed by the septum 3 or the self-sealing separating wall 4.

As shown in FIG. 1A, the self-sealing separating wall 4 is preferably formed in a transport head 7 which can be fitted onto the open end. The sample vessel 1 can be fitted into the transport head 7 with its open end sealed, for which purpose for example an O-ring 8 may be used. The self-sealing separating wall 4 closes an outlet channel 9, which opens into the sample vessel 1.

As an alternative, as shown in FIG. 2A, a lid 10 may be fitted onto the open end of the sample vessel 1. The lid 10 bears in a tight fashion on the sample vessel 1, for which purpose an O-ring 8 may again be provided. The lid 10 has a circular recess in order to expose the septum 3 for piercing with an extraction device (not shown).

As shown in FIG. 1B and FIG. 2B, for the heat treatment of the sample in the sample vessel 1, sample vessel 1 can be inserted into a heating device 11. The sample vessel 1 is exposed to heat only along a sublength of the sample vessel 1, which preferably corresponds to the sublength X. The heating device 11 is preferably configured as a holder 12 comprising an integrated heating element, which is preferably formed as a heating wire coil or heating filament 13, into which the sample vessel 1 can be partially inserted. The heating wire coil 13 encloses the sample vessel 1 for indirect heat transfer only along a subsection, which is filled with the sample. Owing to the filling height of the sample in the sample vessel 1, a heating section is formed, along which the sample in the sample vessel 1 is exposed to heat. Intensive heat transfer passing through the sample is thereby achieved, although only a subsection of the sample vessel 1, in particular the cavity, is exposed to high temperatures.

Preferably, besides in particular the thermal radiation, the sample vessel 1 also transfers heat to the sample through its vessel wall by thermal conduction, i.e. contact with the sample.

The heating wire coil 13 may be preheated before inserting the sample vessel, for example in order to carry out flash pyrolysis. The heating wire coil 13 may also be operated at different temperatures, for example in order to concentrate a liquid sample before pyrolysis in the sample vessel 1.

The sample, which is preferably introduced into the cavity in the form of the shaft 5, is thus exposed to a heat treatment which is applied to the entire circumference of the shaft 5. The heat treatment is restricted to the lower sample compartment 31, while a temperature drop is adjusted in or on the headspace compartment 32 by laying out the length and cross section of the sample vessel 1 along the headspace compartment 32. With a temperature level of the thermal action of up to 1400° C., a temperature drop (for example in the vessel wall of the sample vessel 1) is preferably adjusted to at least 300° C., up to the container opening 6 of the sample vessel 1.

The sample vessel 1 and the heating device 11 form a device for preparing samples for an analysis apparatus of the chromatographic separation technique. The thermochemical reaction is preferably carried out as a pyrolytic decomposition. The thermal breakdown may be carried out in an inert atmosphere, i.e. an inert gas (helium, nitrogen) is introduced into the sample vessel 1. As an alternative, the thermal breakdown may be carried out in the presence of an oxygen or air atmosphere. Such an oxidative pyrolysis delivers a greater proportion of oxidized pyrolysate compounds.

The sample, and subsequently the thermal breakdown products, may be dissolved with or without chemical reaction by reagents injected into the sample vessel 1. The sample vessel 1 is consequently also used to receive liquids for chemical reactions. The sample vessel 1 is therefore also a test tube for chemical reactions, examinations and for storing the sample, specifically before and/or after its thermochemical treatment.

For chromatographic separation, a gas phase may be taken directly from the vapor space above the prepared sample, or the prepared sample may be dissolved in a selectable mobile phase. The mobile phase may in this case be a liquid or a supercritical fluid.

The cavity of the sample vessel 1 is filled on the analytical scale. The sample vessel 1 is to this extent preferably filled (up) at least along a section of the sublength X, i.e. the sample is bounded on the edge by the wall of the sample vessel 1. A filling level in the sample vessel 1 is then essentially reached, so that improved heat transfer from the heating device 11 is achieved. Optionally, more uniform filling may be achieved by a stuffing.

A heating section of the heating device 11 for indirect heat transfer is applied along the filling quantity. The shape of the sample vessel 1 may for this purpose also be formed with a vessel constriction or shaft 5, particularly in the form of a container, besides being formed as a tube or finger. The sample vessel 1 is preferably a container which is tapered at its lower end. The sample vessel 1 is, however, preferably always a hollow vessel which is open on one side and can be closed by a cover (for example an injection stopper, PTFE septum, self-sealing separating wall, etc.). The heating section is restricted to the position which is filled with the sample. The way in which the sample is found in the sample vessel 1 permits high thermal penetration thereof.

According to another exemplary embodiment, which is represented in FIG. 3 and FIG. 4, the sample vessel 1 is a part of a container arrangement, which forms a decentral interface of the analytical sample preparation. The holder provided is a module container 14 which can be closed with a closure cap 17 and in the interior 40 of which the sample vessel 1 is inserted as an insertable container and the lower part 15 of which integrates the heating wire coil 13 into the module container 14.

The container arrangement thus comprises a heatable module container 14 with an integrated heating device 11, into which the sample vessel 1 is inserted releasably as an insertable container. The container arrangement is closed by an injection cover.

A solid or semisolid sample, with which the sample vessel is filled, as well as a liquid concentrated in the sample vessel 1, can be heated to a selectable temperature in order, for example, to carry out pyrolysis. The comments above regarding the configuration of the sample vessel 1 apply here accordingly. As a variant from the first exemplary embodiment, however, the sample vessel 1 is in this case an inner vessel which is inserted releasably into a module container 14 as an outer vessel.

The module container 14 is dimensioned in the manner of a vial and comprises a module container body 16 on which a lower part 15 and an upper (injection) cap 17 are fastened, each preferably releasably. In a receiving space 40 of the module container 14, the sample vessel 1 is provided as an inner vessel. The lower part 15 and the cap 17 can preferably be screwed into or onto the module container body 16.

The lower part 15 contains, on the bottom of the module container 14, the heating device 11 which is arranged on an electrical insulation base part 18 formed in the manner of a holder. To this end, two metal pieces 19 are fastened as heating wire contact with screws 20 on the electrical insulation base part 18. Two metal electrodes 21, 22 are applied in the insulation base part 18, and electrical contacts are established between the metal pieces 19 and the electrodes 21, 22 by metal rods 45, in particular solid copper rods. Electrode 21 is an outer ring electrode and electrode 22 is an inner electrode. The (platinum) heating wire coil 13 is fastened on the metal contact pieces 19 with metal screws 24. The heating wire coil 13 defines a heating section in the axial direction of the module container 14. The heating wire coil 13 is supported along this heating section by a quartz tube 25, which can also establish the axial length of the heating section. The quartz tube 25 to this extent forms a shield, in order to concentrate the heat generated by the heating wire coil 13 onto the heating section.

The lower part 15 furthermore has a small spring 26, by means of which the sample vessel 1 is pressed upward when it is inserted. This blocks the sample vessel 1 with its open end, the container opening 6, against the septum 3 which is placed in the cap 17.

The module container body 16 preferably consists of anodized (approximately 100 μm oxide layer) aluminum and has an internal screw thread 27 on the bottom, into which an external screw thread 28 of the insulation base part 18 can be screwed. The insulation base part 18 thus closes the module container body 16 releasably at the bottom. The module container body 16 preferably consists of a metal or a metal alloy.

The sample vessel 1 preferably consists of quartz, in order to withstand pyrolysis temperatures of up to 1400° C. The preferably tubular sample vessel 1 has, as an insertable container, an upper section which is wider than a lower section which forms the vessel constriction, or the shaft 5. The sample vessel 1 therefore preferably has a taper next to the closed lower end of the sample vessel 1. The sample to be examined is introduced into this lower section. The sample here also preferably forms a core of material to be examined in the shaft 5 as a cavity.

The sample vessel 1 is inserted into the module container body 16 in such a way that the shaft 5 filled with the sample is surrounded by the heating wire coil 13. Along the shaft 5, which receives the sample for example with a filling level column or as an object in one or more pieces, the heating section is applied. It is consequently only the lower section of the sample vessel which is exposed to the high temperatures, in particular high pyrolysis temperatures.

The module container body 16 is closed with the cap 17, which is preferably a screw cap 29 and carries the septum 3. The module container body 16 for this purpose has an external screw thread 30 on its head. The septum 3 makes it possible to introduce a needle of an extraction device (not shown), which may in turn inject a pyrolysis or reaction gas and/or a pyrolysis or reaction liquid into the sample vessel 1. The septum 3 is preferably clad with a polymer coating, for example PTFE, which withstands relatively high temperatures (for example up to 300° C.)

The sample vessel 1 and the module container 14 may be closable by a common cap 17 provided with a septum 3, in such a way that samples can readily be taken by an extraction device from the sample vessel 1 for analytical examination. To this extent, the spring 26 has an advantageous effect because the sample vessel 1 is supported on the lower part 15 and is pressed with a prestress against the septum 3 when the module container 14 is closed. The sample vessel 1 may furthermore be alignable and/or positionable by a container neck of the module container 14 in the receiving space 40 of the module container 14.

The dimensions of the module container body 16 are preferably as follows. The external diameter is 11.5 mm and the height without the screw cap 29 is 32 mm. These dimensions are the same as those of 2 ml containers, which are typically used in chromatography instruments. The screw thread 30 of the module container body 16 fits, for example, with commercially available screw caps, so that these can be used in combination with the module container body 16.

The dimensions of a sample compartment 31 of the insertable sample vessel 1 in the form of the vessel constriction 5 may, for example, be selected as follows. The internal diameter is 1.9 mm and the length (height) is 12.5 mm. The volume is approximately 25 µl. The dimensions of a headspace compartment 32 above the sample compartment 31 (cf. FIG. 3) are for example as follows. The internal diameter is 5 mm and the length (height) is 12.5 mm. The internal volume is preferably from 10 to 250 µl. The headspace compartment 32 may in particular be used as a solvent compartment, in particular after the heat treatment of the sample. The internal dimensions make it possible to insert a needle with ease and inject about 50 to 150 µl of solvent.

Preferred dimensions for the sample compartment 31 are heights of less than 60 to 70% of the total height of the sample vessel 1. The sample vessel 1, which is preferably formed cylindrically, preferably has a diameter of from 4 to 40 mm, in particular from 4 to 10 mm, in the headspace compartment 32 and preferably a diameter of from 1 to 20 mm, in particular from 1 to 5 mm, in the sample compartment 31.

The module container 14 represented in FIG. 3 and FIG. 4, and described above, is a vial with a built-in or integrated heating device 11 and with an insertable inner insert in the form of a sample vessel 1, the filled cavity of which can be heated in the sample compartment 31 by the heating device 11. The heat treatment of a sample is thus carried out decentrally and is decoupled from the chromatographic analysis apparatus.

The heating device 11 may be operated by an external electricity supply. Preferably, for this purpose, the module container 14 is placed on a separate heating base 33. With a simple connection technique, for example spring-loaded contacts, or a plug-in technique, a connection to the electrodes 21, 22 of the lower part 15 of the module container 14 may be provided. The electrodes 21, 22 consequently form connection elements for an external electricity supply and for this purpose are preferably inserted externally into the insulation component 18. The heating base 33 may be mounted on a module container station 34 (cf. FIG. 5).

According to the invention, the power supply for the heating wire coil 13 is based, in the exemplary embodiments shown in FIGS. 1A, 1B, 2A, 2B, 3 and 4, on a constant current control. This constant current control is controlled proportionally by pulse width modulation (PWM), i.e. a higher PWM value gives a higher current. In addition, the temperature of the heating wire coil 13 is proportional to the electric current. By programming a maximum PWM value, the heating increase can be controlled as a function of time. The pulse width modulation optimizes the reproducibility of the heat treatment of the sample in the sample vessel 1.

The principle of heating resistance heating wires is thereby utilized without a different electrical resistance being obtained on account of the fact that the exact mounting of the heating wire coil 13 is defective. This is significant because the total resistance over the entire electric circuit can affect the electric current for a given voltage.

The temperature is preferably controlled by three parameters: a preheating time, a delay time and a heating PWM. The preheating time is the time for which a maximum current is applied to the heating wire coil 13. The temperature obtained after the preheating depends on the duration thereof. No current is applied during the delay time. This delay reduces the temperature exceedance particularly at relatively low temperatures. The heating PWM value is a measure of the current during the heating period.

The initial heating by the heating wire coil 13 can begin relatively slowly, at for example 20 to 50° C./s, and can increase up to 250° C./s. Consequently, only 2 to 3 s are needed to achieve a pyrolysis temperature of, for example, 500° C. The heating time to the pyrolysis temperature is preferably 10 to 30 s.

For evaporation of a, for example, liquid sample in the sample vessel 1 before pyrolysis, an evaporator temperature of, for example, 150 to 250° C. is set by means of the heating wire coil 13. Evaporation and pyrolysis can be carried out in the same sample vessel 1.

The heating wire coil 13 is preferably a platinum heating wire coil.

The sample vessel 1 is formed as an insert for an (outer) vial, which can be inserted into a receiving space 40 of a module container 14, which can be closed with a cap 17, as an (inner) vial. An outer vial with an inner vial is therefore formed, which preferably have a common injection closure.

As shown in FIG. 6, the module container station 34 may be mounted on a commercially available XYZ robot formed with a control unit 44. The module container 14 may be transported by a Z unit 35 from a container holder rack 36 into the module container station 34. After the pyrolysis, solvent may be aspirated with a syringe into the Z unit 35 from a solvent container 37, and injected into the module container 14. After this, the module container may optionally be agitated for better mixing. Lastly, the extract may for example be injected into a loop which is installed on an injection valve 38 for injection into a liquid chromatography system. The module container 14 may thus be integrated as an interface into a robot for the sample preparation and sample delivery in the chromatographic separation technique.

FIG. 5 shows a module container station 34 having the heating base 33 and a flow cell 39, which is for example flushed with an inert gas. This gas may be aspirated with a gas-tight syringe and introduced into the sample vessel 1.

The invention makes it possible to prepare a sample in a container, and this process may be fully automated. According to the invention, the use of different sample vessels 1 does not result in different pyrolysis conditions and consequently does not result in unreproducible pyrograms.

The module container 14 may be used for sequential pyrolysis.

The invention claimed is:

1. A device for carrying out a sample preparation for an analysis apparatus, in particular a chromatograph, comprising:

a sample vessel which can be closed by a self-sealing cover and comprises a sample compartment for receiving a substance to be examined;

a holder which comprises a heating wire coil and into which the sample vessel with its sample compartment can be inserted in order to heat the substance to be examined, further wherein the heating wire coil is operatively connected to an inner electrode and an outer closed metal ring electrode arranged on a bottom of the holder, wherein the inner electrode and the outer closed metal ring electrode are positioned in a common plane, and wherein the outer closed metal ring electrode circumscribes the inner electrode; and a power supply for the heating wire coil, wherein the power supply is based on a constant current control that is controlled proportionally by pulse width modulation.

2. The device as claimed in claim 1, wherein the holder provided is a module container which can be closed with a closure cap and in the interior of which the sample vessel is inserted as an insertable container and in the lower part of which the heating wire coil is integrated into the module container.

3. The device as claimed in claim 2, wherein the power supply of the heating wire coil is provided externally via a connectable heating base.

4. The device as claimed in claim 1, wherein the heating wire coil is a platinum heating wire coil.

* * * * *